United States Patent [19]
Field

[11] Patent Number: 5,681,827
[45] Date of Patent: Oct. 28, 1997

[54] COMPOSITION AND METHOD FOR TREATMENT OF GASTROINTESTINAL DISTRESS

[75] Inventor: Paul Frederick Field, Hull, United Kingdom

[73] Assignee: Reckitt & Colman Products Limited, London, United Kingdom

[21] Appl. No.: 606,198

[22] Filed: Feb. 23, 1996

[30] Foreign Application Priority Data

Mar. 3, 1995 [GB] United Kingdom ............... 9504599

[51] Int. Cl.$^6$ .................. A61K 31/715; A61K 33/00; A61K 33/10

[52] U.S. Cl. ............... 514/54; 514/819; 424/687; 424/717

[58] Field of Search .................. 424/717, 686, 424/677, 687, 689; 514/54, 819

[56] References Cited

U.S. PATENT DOCUMENTS 4,869,902  9/1989  Buehler ........................ 424/686

FOREIGN PATENT DOCUMENTS

| | | |
|---|---|---|
| 0286085 | 10/1988 | European Pat. Off. . |
| A 2 369 843 | 6/1978 | France . |
| A 2 563 108 | 10/1985 | France . |
| 1524740 | 9/1978 | United Kingdom . |
| 2222772 | 3/1990 | United Kingdom . |
| WO 88/00825 | 2/1988 | WIPO . |

OTHER PUBLICATIONS

Abstract of Aust.J.Hosp.Pharm. vol.20(1), 1990 Chan, JG et al., at p. 108.

Abstract of Ailment.Pharmacol.Ther. vol.5(5), 1992. Greaves, JL et al.

*Primary Examiner*—Phyllis G. Spivack
*Attorney, Agent, or Firm*—Fish & Richardson P.C.

[57] ABSTRACT

An aqueous pourable liquid composition is disclosed comprising at least 8% sodium alginate and potassium bicarbonate for use in the treatment of gastrointestinal distress.

12 Claims, No Drawings

COMPOSITION AND METHOD FOR TREATMENT OF GASTROINTESTINAL DISTRESS

This invention relates to the preparation of pourable liquid sodium alginate compositions and in particular to the preparation of such compositions for the treatment of reflux oesophagitis, gastritis, dyspepsia or peptic ulceration, or for use as sustained releasing compositions.

Reflux oesophagitis occurs when small amounts of gastric juice, food and/or bile acids pass into the lower part of the oesophagus and cause oesophageal inflammation accompanied by pain which may manifest itself in the form of heartburn.

One approach to the problem of reflux oesophagitis has been to administer a preparation which on contact with gastric acid generates a carbonated gelatinous foam or raft which floats on the stomach contents. When reflux occurs it is this raft which precedes the stomach contents into the oesophagus, thus protecting the mucosa from further irritation. Known preparations of this type include solid preparations in the form of powder or tablets containing alginic acid, sodium bicarbonate and antacid materials or liquid preparations containing sodium alginate, sodium bicarbonate and calcium carbonate marketed under the name GAVISCON (TM Reckitt & Colman Products Ltd). In our British Patent No. 1524740 we describe such liquid preparations.

GB 1524740 specifies that sodium bicarbonate is used as the effervescent agent to release carbon dioxide on contact with stomach acid, and most similar liquid products also use the sodium salt. Sodium bicarbonate is generally the salt of choice for many reasons, including its taste characteristics, its solubility and its general pharmaceutical acceptability. Other bicarbonates, eg potassium bicarbonate have been avoided in the past because of poor taste characteristics (brackish) and because of potential cardiac problems in high dosages.

A current problem with liquid alginate products of the above type is the size of the dose which must be taken (up to 20 ml four times daily). This results in large volumes of products which are not conveniently portable and which take up a lot of space in pharmacies, warehouses etc.

It is therefore an aim of the invention to provide more concentrated products thereby reducing the relative dosage volume.

On the one hand, we have found that merely doubling the concentration of all ingredients in conventional sodium alginate compositions leads to compositions which are too thick to dispense from a bottle and may even be too thick to comfortably swallow.

On the other hand we have found that reducing the sodium bicarbonate concentrations in such products will reduce the initial viscosity to apparently acceptable levels at which pouring may be achieved. However if the bicarbonate concentrations are reduced too far there will be inadequate carbon dioxide production in the stomach, which will lead to inadequate raft formation.

We have found moreover that the compositions having high concentrations of sodium alginate and low concentrations of sodium bicarbonate have a further serious defect. Their pouring properties are lost if storage temperatures drop too low. Specifically, if such compositions are stored at below 5° C. for 48 hours or more they will remain too thick to pour, even after being restored to room temperature and vigorously shaken. Temperatures of 5° C. or lower are commonly encountered when commercial products are stored for long periods in warehouses or transported over long distances.

We have now unexpectedly found that using potassium bicarbonate in the above compositions alleviates these thickening problems.

According to the invention there is provided the use of potassium bicarbonate for the preparation of an aqueous pourable liquid composition comprising at least 8% w/w sodium alginate for use as a pharmaceutical.

Such aqueous pourable liquid compositions that result are pourable at room temperatures and furthermore this property is regained upon warming following prolonged storage below 5° C. for up to six weeks or more (although reasonably vigorous shaking may be required).

By pourable we mean that the compositions of the invention will flow evenly at room temperature (possibly following reasonably vigorous shaking) such that doses of for example 5 ml may be measured out with reasonable accuracy. For example reproducible doses of as low as 5 ml may be dispensed from screw cap bottles having neck diameters of 1.5 cm, or from squeezable plastic bottles having dispensing outlets as small as 5 mm diameter.

Compositions of the invention, particularly those according to the preferred embodiments are liquid, or become liquid upon vigorous shaking, even after prolonged storage under low temperatures.

Whilst simple numerical viscosity is not an accurate prediction of pourability in the compositions of the invention, a rough guide is that compositions having a viscosity of below 3500 mPa.s are preferred and more preferably compositions having a viscosity of below 2000 mPa.s. For the purposes of this rough test the samples should be shaken vigorously before testing and viscosity should be measured at a shear rate of 10 $Ds^{-1}$ in a Bob and Cup Viscometer. Alternatively, to simulate vigorous shaking, the samples may be sheared at 50 $Ds^{-1}$ in a viscometer before the viscosity is measured.

Sodium alginate mainly comprises the sodium salt of alginic acid which is a mixture of polyuronic acids composed of residues of D-mannuronic and L-guluronic acids. It may be obtained from algae belonging to the order Phaeophycae. Preferably, low viscosity grade sodium alginate is used to prepare the compositions according to the invention. These are grades of sodium alginate for which the viscosity of a 10% weight/volume aqueous solution, when determined on a Brookfield RVT viscometer using spindle number 3 at 20 r.p.m. at 20° C., falls within the range 200–1500 mPa.s. An example of a suitable commercial grade of low viscosity sodium alginate is Protanal LFR 5/60 (Pronova Biopol).

Preferably the sodium alginate has a high guluronic acid content. Guluronic acid content is expressed as gel strength (G). High guluronic acid grades of sodium alginate preferably have gel strengths of at least 10 G.

The concentration of sodium alginate in compositions produced according to the invention is higher than in conventional compositions, i.e. at least 8% w/w. Preferably the concentration is 8 to 14% w/v, more preferably 9 to 14% w/v, even more preferably 10 to 13% w/v and most preferably 10 to 12% w/v.

The concentration of potassium bicarbonate in compositions according to the invention is preferably 0.1 to 5% w/v, more preferably 0.5 to 5% w/v, even more preferably 1 to 3% w/v and most preferably 1.5 to 3% w/v.

Compositions prepared according to the invention may be used in the treatment of reflux oesophagitis, gastritis, dyspepsia or peptic ulceration. They may also be used as carriers of other active ingredients and so act as sustained release compositions, or compositions delivering the actives specifically to the stomach (targeted delivery).

Further according to the invention there is provided a method of treating reflux oesophagitis, gastritis, dyspepsia or peptic ulceration which comprises administration of an orally effective amount of an aqueous pourable liquid composition comprising a) 9 to 14% w/v low viscosity sodium alginate;

b) 0.1 to 5% w/v potassium bicarbonate.

Further according to the invention there is therefore provided a pharmaceutical composition for the treatment of reflux oesophagitis, gastritis, dyspepsia or peptic ulceration, or for use as a sustained releasing or targeted delivery composition, in the form of an aqueous pourable liquid comprising a) 9 to 14 w/v low viscosity grade sodium alginate;

b) 0.1 to 5 w/v potassium bicarbonate.

The compositions of the invention preferably also comprise a suspending agent. Suitable suspending agents include carrageenans, hypromellose, tragacanth, pectin, pregelatinised potato starch, sodium starch glycolate, carbomer or mixtures thereof. Carbomer is a synthetic high molecular weight polymer of acrylic acid cross linked with either allyl esters of sucrose or pentaerythritol. Suitable commercially available grades of carbomer include Carbopol 934P or Carbopol 974P (BF Goodrich).

For use in liquid products, carbomers must be neutralised after being pre-dispersed in water. The preferred neutralising agent is sodium hydroxide. The concentration of carbomer is given as the total amount of material used before neutralisation.

The choice of suspending agent and its concentration will depend upon the amount and grade of sodium alginate used in the compositions and upon the amount and type of extra insoluble ingredients used. Preferably the suspending agent is a carbomer. The preferred concentration of suspending agent is 0.1 to 1% w/v, most preferably 0.1 to 0.5% w/v.

The compositions of the present invention preferably further comprise a source of divalent or trivalent metal ions to strengthen the raft formed in the stomach. These metal ions preferably become available when the compositions reach the stomach but must not be available before then or the compositions will gel too early. Suitable metal ions are aluminium and, preferably, calcium ions. Most preferably the compositions comprise calcium carbonate.

The compositions of the present invention therefore preferably further comprise from 0.1 to 5% w/v calcium ions, most preferably 0.5 to 3% w/v calcium carbonate.

Still further according to the invention, there is provided a pharmaceutical composition for the treatment of reflux oesophagitis, gastritis, dyspepsia or peptic ulceration, or for use as a sustained releasing or targeted delivery composition, in the form of an aqueous pourable liquid comprising a) 8 to 14 w/v low viscosity sodium alginate;

b) 0.1 to 5 w/v potassium bicarbonate;

c) 0.1 to 1% w/v carbomer, neutralised with sodium hydroxide; and d) 0 to 5% w/v, preferably 0.5 to 5% w/v, calcium carbonate.

The compositions of the present invention preferably comprise substantially no source of sodium ions other than those provided by the sodium alginate and the sodium hydroxide used to neutralise the carbomer. Most preferably no sodium bicarbonate is added during the manufacture of the compositions of the invention.

The compositions of the present invention may further comprise preservatives to prevent contamination and subsequent deterioration by micro-organisms. Examples of suitable preservatives are methyl, ethyl, propyl and butyl parahydroxybenzoates and their salts, which are preferably used in combination eg methyl and propyl or ethyl and butyl.

Preferred concentrations for the preservatives are 0.01 to 0.5% w/v.

The compositions of the present invention may also include one or more of the following ingredients, colouring, sweetening, flavouring or pH adjusting ingredients.

Where the compositions of the present invention are intended for use as sustained releasing compositions they will also contain active ingredients suitable for sustained administration in the stomach.

Where the compositions of the present invention are intended for use as targeted delivery compositions they will also contain active ingredients suitable for specific delivery to the stomach, for example local antimicrobial agents.

The compositions of the invention may be prepared by any conventional manufacturing process for compositions of this type. Preferably the compositions are prepared by the following process.

1) Dissolving the potassium bicarbonate in approximately 60% of the water to be used in the composition and mixing in any of the preservatives, sweeteners and crosslinking aids (if used).

2) Adding the sodium alginate and stirring until dissolved.

3) Adding the suspending agents (if used). If the suspending agent is carbomer it should be pre neutralised with sodium hydroxide in approximately 30% of the water to be used in the compositions.

4) Adding any flavourings or colouring agents and adjusting the volume.

The process is preferably carried out at approximately 20° to 25° C.

The invention will now be illustrated by reference to the following examples.

EXAMPLE 1

Sodium alginate LFR 5/60 100 g (Pronova Biopol)

Potassium bicarbonate 20 g

Calcium carbonate 20 g

Carbomer (Carbopol 974P) 1 g

Sodium hydroxide 0.3 g

Ethyl parahydroxybenzoate 2 g

Sodium butyl parahydroxybenzoate 0.2 g

Sodium Saccharin 2 g

Flavour 2 g

Deionised water to 1 liter

1. The carbomer was dispersed in 300 ml deionised water in a first vessel and neutralised with the sodium hydroxide.
2. In a second vessel the potassium bicarbonate, calcium carbonate, preservatives and saccharin were mixed with 600 ml deionised water.
3. The sodium alginate was added to the second vessel and stirred until fully dissolved.
4. The contents of the second vessel were added to the contents of the first vessel and stirred until fully dispersed.
5. The flavour was added and the volume adjusted to 1 liter by the addition of further deionised water. The mixture was stirred until fully dispersed.

EXAMPLES 2 TO 12

The following further Examples were all produced by the method of Example 1.

|  | 2 | 3 | 4 | 5 | 6 |
|---|---|---|---|---|---|
| Sodium alginate LFR 5/60 (Pronova Biopol) | 100 g | 100 g | 100 g | 100 g | 100 g |
| Potassium bicarbonate | 20 g | 31 g | 31 g | 31 g | 31 g |
| Calcium carbonate | 20 g | 32 g | 32 g | 32 g | 32 g |
| Carbomer (Carbopol 974P) | 2 g | 2 g | 4 g | 6 g | 1 g |
| Sodium hydroxide | 0.7 g | 0.7 g | 1.4 g | 2.1 g | 0.3 g |
| Ethyl parahydroxybenzoate | 2 g | 2 g | 2 g | 2 g | 2 g |
| Sodium butyl parahydroxybenzoate | 0.2 g | 0.2 g | 0.2 g | 0.2 g | 0.2 g |
| Sodium Saccharin | 2 g | 2 g | 2 g | 2 g | 2 g |
| Flavour | 2 g | 2 g | 2 g | 2 g | 2 g |
| Deionised Water to | 1 ltr | 1 ltr | 1 ltr | 1 ltr | 1 ltr |

|  | 7 | 8 | 9 |
|---|---|---|---|
| Sodium alginate LFR 5/60 (Pronova Biopol) | 100 g | 100 g | 100 g |
| Potassium bicarbonate | 20 g | 10 g | 25 g |
| Calcium carbonate | 32 g | 32 g | 32 g |
| Carbomer (Carbopol 974P) | 2 g | 2 g | 2 g |
| Sodium hydroxide | 0.7 g | 0.7 g | 0.7 g |
| Ethyl parahydroxybenzoate | 2 g | 2 g | 2 g |
| Sodium butyl parahydroxybenzoate | 0.2 g | 0.2 g | 0.2 g |
| Sodium saccharin | 2 g | 2 g | 2 g |
| Flavour | 2 g | 2 g | 2 g |
| Deionised Water to | 1 ltr | 1 ltr | 1 ltr |

|  | 10 | 11 | 12 |
|---|---|---|---|
| Sodium alginate LFR 5/60 (Pronova Biopol) | 100 g | 100 g | 100 g |
| Potassium bicarbonate | 31 g | 31 g | 31 g |
| Calcium carbonate | 16 g | 8 g | 24 g |
| Carbomer (Carbopol 974P) | 1 g | 1 g | 1 g |
| Sodium hydroxide | 0.3 g | 0.3 g | 0.3 g |
| Ethyl parahydroxybenzoate | 2 g | 2 g | 2 g |
| Sodium butyl parahydroxybenzoate | 0.2 g | 0.2 g | 0.2 g |
| Sodium saccharin | 2 g | 2 g | 2 g |
| Flavour | 2 g | 2 g | 2 g |
| Deionised Water to | 1 ltr | 1 ltr | 1 ltr |

Examples 2 to 12 may be repeated using 8 or 12% w/v sodium alginate instead of 10%.

Examples 2 to 12 may further be repeated using 0.5, 4 or 5% w/v potassium bicarbonate.

All of Examples 1 to 12 have the capability of being stored for at least 48 hours below 4° C., and in the case where a gel forms can be made pourable at room temperature by reasonable shaking or stirring.

EXAMPLES 13 TO 24

|  | 13 | 14 | 15 | 16 |
|---|---|---|---|---|
| Sodium alginate LFR 5/60 (Pronova Biopol) | 100 g | 80 g | 100 g | 100 g |
| Potassium bicarbonate | 20 g | 20 g | 10 g | 15 g |
| Calcium carbonate | 20 g | 20 g | 20 g | 20 g |
| Aluminium hydroxide | — | — | — | — |
| Carbomer (Carbopol 974P) | 4 g | 4 g | 4 g | 4 g |
| Sodium hydroxide | 1.4 g | 1.4 g | 1.4 g | 1.4 g |
| Ethyl parahydroxybenzoate | 2 g | 2 g | 2 g | 2 g |
| Sodium butyl parahydroxybenzoate | 0.22 g | 0.22 g | 0.22 g | 0.22 g |
| Sodium saccharin | 1 g | 1 g | 1 g | 1 g |
| Flavour | 0.7 g | 0.7 g | 0.7 g | 0.7 g |
| Deionised water to | 1 ltr | 1 ltr | 1 ltr | 1 ltr |

|  | 17 | 18 | 19 | 20 |
|---|---|---|---|---|
| Sodium alginate LFR 5/60 (Pronova Biopol) | 100 g | 100 g | 100 g | 100 g |
| Potassium bicarbonate | 20 g | 20 g | 20 g | 20 g |
| Calcium carbonate | — | — | 20 g | 20 g |
| Aluminium hydroxide | — | 20 g | — | — |
| Carbomer (Carbopol 974P) | 4 g | 4 g | 4 g | — |
| Sodium hydroxide | 1.4 g | 1.4 g | 1.4 g | — |
| Ethyl parahydroxybenzoate | 2 g | 2 g | 5 g | 2 g |
| Sodium butyl parahydroxybenzoate | 0.22 g | 0.22 g | 0.55 g | 0.22 g |
| Sodium saccharin | 1 g | 1 g | 1 g | 1 g |
| Flavour | 0.7 g | 0.7 g | 0.7 g | 0.7 g |
| Deionised water to | 1 ltr | 1 ltr | 1 ltr | 1 ltr |

|  | 21 | 22 | 23 | 24 |
|---|---|---|---|---|
| Sodium alginate LFR 5/60 (Pronova Biopol) | 120 g | 130 g | 100 g | 100 g |
| Potassium bicarbonate | 20 g | 20 g | 5 g | 50 g |
| Calcium carbonate | — | — | 20 g | 20 g |
| Aluminium hydroxide | — | — | — | — |
| Carbomer (Carbopol 974P) | 4 g | 4 g | 4 g | 4 g |
| Sodium hydroxide | 1.4 g | 1.4 g | 1.4 g | 1.4 g |
| Ethyl parahydroxybenzoate | 2 g | 2 g | 2 g | 2 g |
| Sodium butyl parahydroxybenzoate | 0.22 g | 0.22 g | 0.22 g | 0.22 g |
| Sodium saccharin | 1 g | 1 g | 1 g | 1 g |
| Flavour | 0.7 g | 0.7 g | 0.7 g | 0.7 g |
| Deionised water to | 1 ltr | 1 ltr | 1 ltr | 1 ltr |

Each of Examples 13 to 24 were manufactured by the general method of Example 1 (taking into account changes necessitated by the various formula differences).

Samples of each of Examples 13 to 24 were stored at 4° C. for 3 weeks and were all found to be easily pourable following warming to room temperature and shaking.

What is claimed is:

1. A pharmaceutical composition for the treatment of reflux esophagitis, gastritis, dyspepsia or peptic ulceration, or for use as a sustained releasing or targeted delivery composition, in the form of an aqueous pourable liquid comprising a) 8 to 14% w/v low viscosity grade sodium alginate;

b) 0.1 to 5% w/v potassium bicarbonate.

2. A pharmaceutical composition according to claim 1 which contains a suspending agent, selected from carrageenans, hypromellose, tragacanth, pectin, pregelatinised potato starch, sodium starch glycolate, carbomer and mixtures thereof.

3. A pharmaceutical composition according to claim 1 which contains a source of divalent or trivalent metal ions to strengthen the raft formed in the stomach.

4. A pharmaceutical composition for the treatment of reflux esophagitis, gastritis, dyspepsia or peptic ulceration, or for use as a sustained releasing or targeted delivery composition, in the form of an aqueous pourable liquid comprising a) 8 to 14% w/v low viscosity sodium alginate;
 b) 0.1 to 5% w/v potassium bicarbonate;
 c) 0.1 to 1% w/v carbomer, neutralized with sodium hydroxide; and
 d) 0 to 5% w/v, calcium carbonate.

5. A pharmaceutical composition according to claim 4 which comprises:

a) 8–13% w/v low viscosity sodium alginate;
 b) 0.5–5% w/v potassium bicarbonate;
 c) 0.1–0.6% w/v carbomer, neutralized with sodium hydroxide; and,
 d) 0.8–3.2% w/v calcium carbonate.

6. A pharmaceutical composition according to claim 5 which further comprises at least one of:

sodium hydroxide, ethyl parahydroxybenzoate, sodium butyl parahydroxybenzoate sodium saccharin, and a flavoring agent.

7. A pharmaceutical composition according to claim 5 which comprises:

a) 8.7% w/v low viscosity sodium alginate;
 b) 1.7% w/v potassium bicarbonate;
 c) 0.34% w/v carbomer, neutralized with sodium hydroxide; and,
 d) 1.7% w/v calcium carbonate.

8. A pharmaceutical composition according to claim 7 which further comprises at least one of:

sodium hydroxide, ethyl parahydroxybenzoate, sodium butyl parahydroxybenzoate, sodium saccharin, and a flavoring agent.

9. The pharmaceutical composition of claim 4 comprising 0.5 to 5% w/v calcium carbonate.

10. A method of treating reflux esophagitis, gastritis, dyspepsia or peptic ulceration which comprises administration of an orally effective amount of an aqueous pourable liquid composition comprising a) 8 to 14% w/v low viscosity sodium alginate;
 b) 0.1 to 5% w/v potassium bicarbonate.

11. A method according to claim 10 which comprises administration of an orally effective amount of an aqueous pourable liquid composition comprising:

a) 8–13% w/v low viscosity sodium alginate;
 b) 0.5–5% w/v potassium bicarbonate;
 c) 0.1–0.6% w/v carbomer, neutralized with sodium hydroxide; and,
 d) 0.8–3.2% w/v calcium carbonate.

12. The method according to claim 11 wherein the composition further comprises at least one of:

sodium hydroxide, ethyl parahydroxybenzoate, sodium butyl parahydroxybenzoate, sodium saccharin, and a flavoring agent.

* * * * *